(12) United States Patent
Bejarano

(10) Patent No.: US 10,898,362 B2
(45) Date of Patent: Jan. 26, 2021

(54) ORTHOSIS, RELATED COMPONENTS AND METHODS OF USE

(71) Applicant: DJO, LLC, Vista, CA (US)

(72) Inventor: Robert Bejarano, Carlsbad, CA (US)

(73) Assignee: DJO, LLC, Vista, CA (US)

(*) Notice: Subject to any disclaimer, the term of this patent is extended or adjusted under 35 U.S.C. 154(b) by 333 days.

(21) Appl. No.: 15/863,589

(22) Filed: Jan. 5, 2018

(65) Prior Publication Data

US 2018/0193180 A1 Jul. 12, 2018

Related U.S. Application Data

(60) Provisional application No. 62/443,572, filed on Jan. 6, 2017.

(51) Int. Cl.
*A61F 5/01* (2006.01)
*A61F 5/058* (2006.01)
*A61F 5/37* (2006.01)

(52) U.S. Cl.
CPC ........ *A61F 5/0102* (2013.01); *A61F 5/05858* (2013.01); *A61F 5/3753* (2013.01); *A61F 2005/0158* (2013.01); *A61F 2005/0167* (2013.01)

(58) Field of Classification Search
CPC .. A61F 5/05858; A61F 5/3753; A61F 5/0118; A61F 5/013; A61F 5/3738; A61F 5/3715; A61F 5/01; A61F 5/37373; A61F 2005/0158; A61F 2005/0167; A61F 2005/0132; A61F 2005/0151; A61F 2005/0153; A61F 2005/0165; A61H 1/02; A61H 1/0274; A61H 1/0277; A61H 1/0281; A61H 2201/0173; A61H 2201/1614; A61H 2201/1635; A61H 2201/135; A61G 7/05; A61G 7/075; A61G 7/0755; A61G 7/065; A61G 13/1235; A61G 13/1255;
(Continued)

(56) References Cited

U.S. PATENT DOCUMENTS 2,310,566 A * 2/1943 Anderson ............. A61F 5/3753
602/19
4,817,588 A * 4/1989 Bledsoe ................ A61F 5/0125
602/16
(Continued)

FOREIGN PATENT DOCUMENTS

WO 2009111378 A2 9/2009

OTHER PUBLICATIONS

STIC Search Results Conducted by Fern Birtwistle Feb. 26, 2020 (Year: 2020).*
(Continued)

*Primary Examiner* — Alireza Nia
*Assistant Examiner* — Daniel A Miller
(74) *Attorney, Agent, or Firm* — Veros Legal Solutions, LLP

(57) ABSTRACT

An orthosis, and components thereof, that may be used as a shoulder brace for immobilization of the arm and shoulder joint may comprise components that may allow for abduction, internal/external rotation and allow for flexion and extension simultaneously. Methods of using the brace and methods of using the brace and treating shoulder injuries are similarly provided.

20 Claims, 15 Drawing Sheets

(58) Field of Classification Search
CPC .. A61G 13/10; A61G 13/12; Y10T 16/54028; Y10T 403/32196; E05D 11/1028
USPC .................................................. 602/5, 16, 20
See application file for complete search history.

(56) References Cited

U.S. PATENT DOCUMENTS

| | | | | |
|---|---|---|---|---|
| 5,086,760 | A * | 2/1992 | Neumann | A61F 5/0123 |
| | | | | 602/16 |
| 5,407,420 | A * | 4/1995 | Bastyr | A61F 5/013 |
| | | | | 602/16 |
| 5,487,724 | A * | 1/1996 | Schwenn | A61F 5/3753 |
| | | | | 602/20 |
| 6,533,741 | B1 * | 3/2003 | Lee | A61F 5/05858 |
| | | | | 128/878 |
| 6,589,195 | B1 * | 7/2003 | Schwenn | A61F 5/0125 |
| | | | | 602/16 |
| 6,827,653 | B2 * | 12/2004 | Be | A63B 71/148 |
| | | | | 2/161.1 |
| 2006/0218749 | A1 * | 10/2006 | Brown | E05D 11/1042 |
| | | | | 16/332 |
| 2007/0225620 | A1 * | 9/2007 | Carignan | B25J 9/0006 |
| | | | | 601/5 |
| 2010/0174220 | A1 | 7/2010 | Fout et al. | |
| 2011/0009786 | A1 * | 1/2011 | Chan | A61F 5/0125 |
| | | | | 602/16 |
| 2011/0314637 | A1 | 12/2011 | Bejarano et al. | |

OTHER PUBLICATIONS

International Search Report and Written Opinion in International Patent Application No. PCT/US2018/012621, dated Jul. 4, 2018.

* cited by examiner

ORTHOSIS, RELATED COMPONENTS AND METHODS OF USE

CROSS-REFERENCE TO RELATED APPLICATION

This application claims the benefit of U.S. Provisional Application No. 62/443,572, filed Jan. 6, 2017, the entire contents of which are hereby incorporated by reference in their entirety herein.

BACKGROUND

Field of the Disclosure

Injuries to the arm and shoulder require various braces that allow for various movement to provide a therapeutic angle or to prevent atrophy. When a patient is required to abduct the affected arm relative to the sagittal plane, some braces require separate bulky wedge(s) or pillows to vary the abduction angle, which is cumbersome. Some braces may be equipped to fix the angle at only a certain number of angles without the flexibility to choose an angle that may be best for the patient. Other braces include a bendable metal part that can be deformed to a required therapeutic angle but which may fatigue and crack over time and may prevent the user from achieving the required therapeutic angle. Bendable metal may also be unstable at larger angles and may require the use of wedges or pillows to keep a therapeutic angle in a fixed position.

Similarly, when a patient is required to internally or externally rotate the affected forearm relative the sagittal plane, wedges, pillows or a bendable metal may be used to provide an internal/external rotation angle but the metal may similarly fatigue over time.

For patients who require their shoulder to be immobilized due to shoulder injuries, slings are not equipped to immobilize the shoulder, that is, to prevent shoulder flexion and extension. Slings also prevent a patient from performing exercises, such as forearm flexion and extension, to prevent atrophy while immobilizing the shoulder to prevent shoulder flexion and extension. If the sling is removed to perform range of motion or pendulum exercises, the shoulder may move to an undesirable position.

Simultaneously accommodating movements such as abduction, internal and external rotation, and flexion and extension while immobilizing the shoulder may require multiple devices. In addition, different braces may be necessary to accommodate either a left or a right arm. Various size patients need various sized braces to accommodate, for example, various arm lengths, torso sizes, and heights. Further, some braces have screws and other fasteners that require using tools to adjust the size of the brace, which is cumbersome and difficult for patients having the use of only one unaffected arm.

Moreover, when a patient does not have the use of an arm, difficulty arises when attempting to position an orthosis having the use of a single unaffected arm, without the help of another person.

It would be useful in the art to overcome one or more of the aforementioned problems.

SUMMARY

According to some embodiments, a lockable orthosis assembly is provided. The lockable orthosis assembly includes an internal/external rotation pivot hub defining an axial hub opening. The lockable orthosis assembly includes a hub base plate defining a plate opening, the hub base plate pivotally engaged with the internal/external rotation pivot hub. The lockable orthosis assembly includes a panel defining a panel opening and having at least one hub base plate adjustment receiver proximate the panel opening. The lockable orthosis assembly includes a hub lock knob defining a mating opening. The lockable orthosis assembly includes a hub lock down axially disposed through the axial hub opening, the plate opening, and the panel opening. The hub lock down includes a mating end mated to the mating opening of the hub lock knob. The panel is disposed between the hub base plate and the hub lock knob. An assembly of the hub lock down, internal/external rotation pivot hub, hub base plate, and hub lock knob is translatably engaged through the panel opening of the at least one hub base plate adjustment receiver of the panel.

The hub base plate may further include a slide member. The panel may further include at least one hub base plate adjustment receiver proximate said hub lock knob. The lockable orthosis assembly may further include a lower hub washer disposed between the panel and the hub lock knob. In some aspects, the lockable orthosis assembly may further include a washer proximate a distal end of the hub lock knob. The internal/external rotation pivot hub may further define, in some aspects, a plurality of teeth pivotally engaged to a plurality of opposing teeth defined in the hub base plate. The hub lock knob may further include unidirectional gear teeth; wherein the lower hub washer is has a key portion. The internal/external rotation pivot hub may be a ball in some aspects. Further, the hub base plate may be a socket base. The hub lock knob may be a locking torque knob. The hub lock down may be a lock down screw. When in use, the internal/external rotation pivot hub may pivotally engage the hub base plate and may be lockable at any one of a plurality of predetermined indexing points or friction interface.

A multi pivoting interface may include in some aspects the lockable orthosis assembly herein and may further include an upper arm support coupled to the hub lock down; and a forearm support rotationally engaged with the upper arm support wherein at least a portion of the forearm support is disposed between the upper arm support and the internal/external rotation pivot hub. For example, according to some aspects, the multi pivoting interface includes a lockable orthosis assembly including an internal/external rotation pivot hub defining an axial hub opening. The assembly includes a hub base plate defining a plate opening, the hub base plate pivotally engaged with the internal/external rotation pivot hub. The assembly includes a panel defining a panel opening and having at least one hub base plate adjustment receiver proximate the panel opening. The assembly includes a hub lock knob defining a mating opening. The assembly includes a hub lock down axially disposed through the axial hub opening, the plate opening, and the panel opening, the hub lock down including a mating end mated to the mating opening of the hub lock knob. The panel is disposed between the hub base plate and the hub lock knob. An assembly of the hub lock down, the internal/external rotation pivot hub, the hub base plate, and the hub lock knob is translatably engaged through the panel opening of the at least one hub base plate adjustment receiver of the panel. The multi pivoting interface includes an upper arm support coupled to the hub lock down. The multi pivoting interface includes a forearm support rotationally engaged with the upper arm support wherein at least a portion of the forearm support is disposed between the upper arm support and the internal/external rotation pivot hub.

The hub lock down may be at least partially recessed in the axial hub opening. In some aspects, the upper arm support may be coupled by a rivet to the hub lock down. The internal/external rotation pivot hub may further define at least one perpendicular hub opening. The upper arm support may have an upper arm support hub end defining at least one perpendicular arm support opening. The at least one perpendicular hub opening and the at least one perpendicular arm support opening may be aligned in some aspects. The rivet may be disposed through the at least one perpendicular hub opening and the at least one perpendicular arm support opening.

In some aspects, the multi pivoting interface may include an arm brace lock longitudinally disposed within the forearm support. The forearm support may include a forearm support hub end defining a forearm hub lock opening. The upper arm support may include an upper arm support hub end defining at least one arm support hub lock opening. In some aspects, the arm brace lock may be releasably engaged with the forearm support through the forearm hub lock opening and the upper arm support through the at least one arm support hub lock opening.

In some aspects, the multi pivoting interface may further include a wrist support assembly adjustably engaged with the forearm support. The wrist support assembly may include at least one wrist bar retractably engaged with the forearm support, and a wrist shell removeably engaged with the at least one wrist bar. The multi pivoting interface may further include, in some aspects, a lock switch transversely aligned with the longitudinal axis of the at least one wrist bar and moveably engaged with the arm brace lock. The multi pivoting interface may further include a stay and a fastener, such as a rivet and a washer, and the wrist shell may be fastened to the stay with the fastener. The stay may define a fastener opening. The wrist shell may define a rivet opening and a stay opening. The rivet may be disposed through the fastener opening of the stay and the rivet opening. In some aspects, the multi pivoting interface may further include a forearm cover at least partially enclosing the arm brace lock between the forearm cover and a distal end of the forearm support.

In some embodiments, an orthopedic shoulder device may include the multi pivoting interface herein. The panel may be an abduction support panel and the device may further include a rigid hinged frame including the abduction support panel coupled to a torso support panel through a locking abduction hinge, such as a positive locking hinge. For example, the orthopedic shoulder device includes a multi pivoting interface including a lockable orthosis assembly including an internal/external rotation pivot hub defining an axial hub opening. The assembly includes a hub base plate defining a plate opening, the hub base plate pivotally engaged with the internal/external rotation pivot hub. The assembly includes a panel defining a panel opening and having at least one hub base plate adjustment receiver proximate the panel opening. The assembly includes a hub lock knob defining a mating opening. The assembly includes a hub lock down axially disposed through the axial hub opening, the plate opening, and the panel opening, the hub lock down including a mating end mated to the mating opening of the hub lock knob. The panel is disposed between the hub base plate and the hub lock knob. An assembly of the hub lock down, the internal/external rotation pivot hub, the hub base plate, and the hub lock knob is translatably engaged through the panel opening of the at least one hub base plate adjustment receiver of the panel. The multi pivoting interface includes an upper arm support coupled to the hub lock down. The multi pivoting interface includes a forearm support rotationally engaged with the upper arm support wherein at least a portion of the forearm support is disposed between the upper arm support and the internal/external rotation pivot hub. The orthopedic shoulder device includes a rigid hinged frame including the abduction support panel coupled to a torso support panel through a locking abduction hinge.

The locking abduction hinge may include a torso hinge releasably engaged with a lock shaft on a first distal end of the locking abduction hinge. The locking abduction hinge may include a free rotation hinge on a second distal end of the locking abduction hinge. The torso hinge and the lock shaft may be axially aligned with the free rotation hinge. The locking abduction hinge may include at least a portion of a spring may be axially disposed between the lock shaft and the free rotation hinge.

The locking abduction hinge may include a right torso hinge releasably engaged with a right lock shaft on a right distal end of the locking abduction hinge. The locking abduction hinge may include a left torso hinge releasably engaged with a left lock shaft on a left distal end of the locking abduction hinge, The left torso hinge and the left lock shaft may be axially aligned with the right torso hinge and the right lock shaft. The locking abduction hinge may include at least a portion of at least one spring may be axially disposed between the right lock shaft and the left lock shaft.

In some aspects, the orthopedic shoulder device may include an edge of the abduction support panel that defines an axial edge opening and opposing edge teeth on at least one end of the axial edge opening and may be axially aligned with the lock shaft. The torso hinge may define a torso hinge opening and torso hinge opposing teeth. The lock shaft may define shaft teeth engagingly coupled to the opposing edge teeth and the torso hinge opposing teeth.

In some aspects, the orthopedic shoulder device may include an edge that defines a right edge opening and right opposing edge teeth, and a left edge opening and left opposing edge teeth on each end of the axial edge opening. The torso hinge may define a right torso hinge opening and right torso hinge opposing teeth, and a left torso hinge opening and left torso hinge opposing teeth. A right lock shaft may define right shaft teeth engagingly coupled to the right opposing edge teeth and the right torso hinge opposing teeth. A left lock shaft may define left shaft teeth engagingly coupled to the left opposing edge teeth and the left torso hinge opposing teeth.

The torso support panel may define a right perpendicular opening on a right end of the torso support panel and a left perpendicular opening on a left end of the torso support panel; the right torso hinge may further define a right protrusion disposed within the right perpendicular opening; and the free rotation hinge further may define a left protrusion disposed within the left perpendicular opening.

The torso support panel may define a right perpendicular opening on a right end of the torso support panel and a left perpendicular opening on a left end of the torso support panel, the right torso hinge further may define a right protrusion disposed within the right perpendicular opening; and the left torso hinge further may define a left protrusion disposed within the left perpendicular opening. The torso support panel may include an alterable distal end.

In some aspects, the orthopedic shoulder device may further include a vest at least partially enclosing the torso support panel and having an adjustable belt and/or may further include an upper arm support cover at least partially enclosing the upper arm support; a forearm support cover least partially enclosing the forearm support; an upper arm securing member secured to the upper arm support cover; and a forearm securing member secured to the forearm support cover.

In some aspects, the orthopedic shoulder device may further include a wrist assembly cover at least partially enclosing the wrist assembly; and a hand securing member secured to the wrist assembly cover. In some aspects, the orthopedic shoulder device may further include a condyle cover at least partially covering the upper arm support hub end or the forearm support hub end.

Methods may include using the lockable orthosis assembly herein. In some aspects, a method may include locking a position of the internal/external rotation pivot hub in the hub base plate at a selected angle, and sliding the at least one slide member along the at least one hub base plate adjustment receiver of the panel. The methods may further include rotating the forearm support hub end in relation to the upper arm support hub end to position an angle between the upper arm support and the forearm support, and locking the forearm support at a selected angle. The rotating step may further include accommodating an angle useful for an opposite arm. The method may further include adjusting the wrist support assembly to a retracted or extended position.

In some aspects, the method of using the orthopedic shoulder brace may include adjusting the locking abduction hinge; and locking the locking abduction hinge at a selected angle between the abduction support panel and the torso support panel. In some aspects, the method of using the orthopedic shoulder includes positioning the orthopedic shoulder brace on a patient, using only an uninjured arm in the positioning step.

Other features and advantages will be apparent from the following detailed description, the drawings, and the claims.

DETAILED DESCRIPTION

Figure 1:
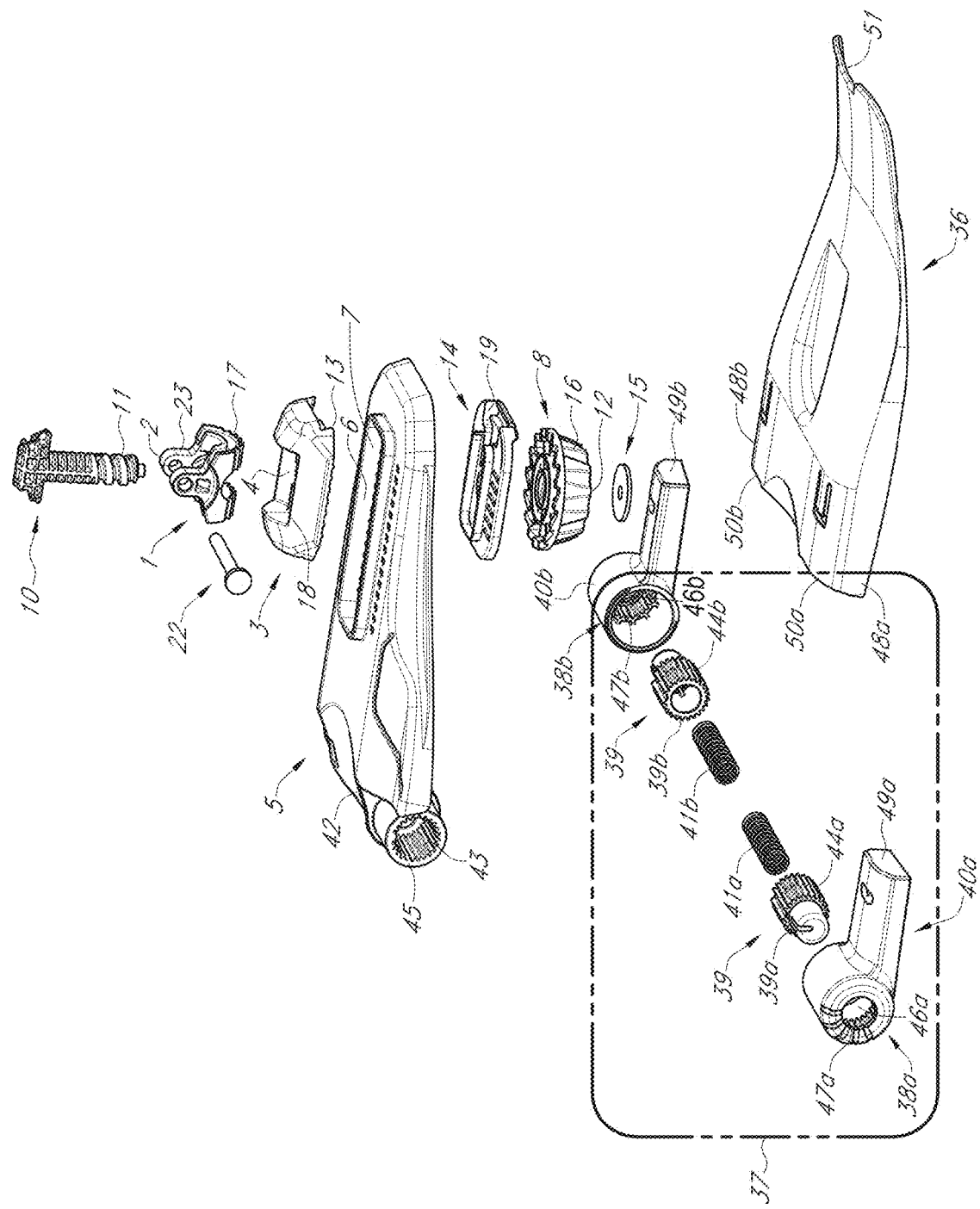
FIG. 1 illustrates an exploded view including the hinged abduction assembly, the pivot assembly, and an aspect for accommodating various arm lengths, according to some example embodiments.

Aspects of the present orthosis may overcome at least some or all of the problems associated with conventional shoulder braces. In one aspect, the shoulder brace or orthosis herein provides shoulder immobilization to aid in post-surgical rehabilitation involving the affected shoulder joint. In one embodiment, the orthosis is designed to provide the ability to perform one or more of the following functions: a) provide the patient the ability to abduct the affected arm relative to the sagittal plane of the individual from about 0° (neutral) to 90°, in pre-determined increments, in some aspects without the use of separate bulky wedges or bendable metal to obtain the angle; b) provide internal rotation of the forearm relative to the sagittal plane of the individual in predetermined increments, in some aspects without the use of bendable metal to obtain the angle; c) provide external rotation of the forearm relative to the sagittal plane of the individual in predetermined increments; and/or provide forearm flexion and extension mobility while the shoulder brace is positioned on the individual, in some aspects while immobilizing the shoulder (i.e., preventing shoulder flexion or extension) so that lower arm movement or exercise may be performed.

In some embodiments, multiple pathologies can be addresses with one orthosis, including, but not limited to: glenohumeral dislocation or subluxation, capsular shifts, posterior shoulder stabilizations, Bankart repairs, release severe anterior capsule contracture, soft tissue strains or repairs, rotator cuff repairs, total shoulder replacement, superior labral repairs (SLAP), shoulder debridement, fractures (humerus, elbow, forearm), biceps tendon repair, elbow ligament/tendon repair, anterior shoulder lauxation and AC joint reconstruction.

The patient may be required to perform internal or external rotation of the forearm during rehabilitation. In one embodiment, an assembly may provide a brace or a portion of a brace that will have a mechanism that allows internal and external rotation and at the same time allowing the brace to be adjusted to fit a patient's arm length as the upper arm length varies from person to person. The same brace has, in some aspects, the ability to adjust to accommodate various arm lengths.

Turning to the drawings, wherein like reference numerals refer to like elements, techniques of the present disclosure are illustrated as being implemented in a suitable environment. The following description is based on embodiments of the claims and should not be taken as limiting the claims with regard to alternative embodiments that are not explicitly described herein.

Figure 6:
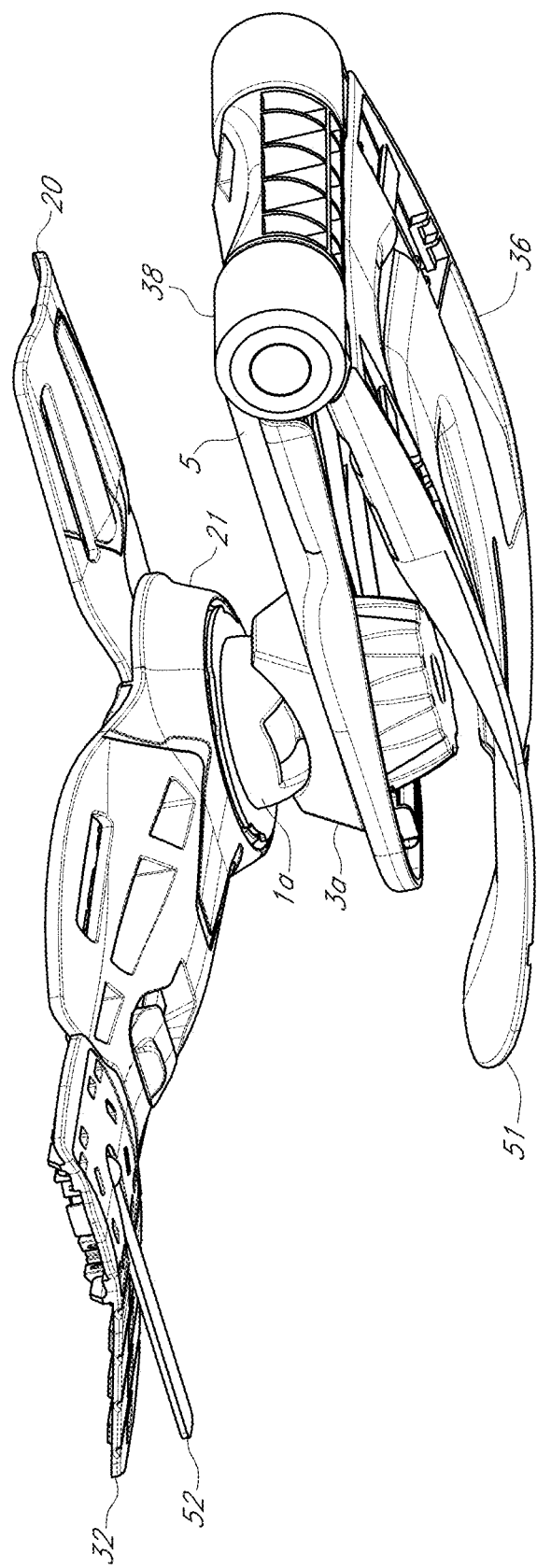
FIG. 6 illustrates a perspective view including a ball and socket interface, according to some example embodiments.

With reference to FIG. 1, an internal/external rotation pivot hub 1 defines an axial hub opening 2 and is pivotally engaged with a hub base plate 3 that defines a plate opening 4. The assembly allows for lockable adjustment when performing internal or external rotation of the forearm. The internal/external rotation pivot hub 1, in some aspects, may define a plurality of teeth 17 pivotally engaged to a plurality of opposing teeth 18 defined in the hub base plate 3. This embodiment provides the ability for adjustment at predetermined intervals or angles (i.e., indexing points). The teeth or slots may be indexed at various angles such as 15° each to internally or externally rotate 15°, 30°, or 45°. Microindexing or infinite indexing is difficult but not impossible to achieve with teeth or slots because the material to make the teeth or slots must be made thinner to accommodate smaller angle changes and the material may become weaker. Angular displacement may also be achieved with a hinge. Alternatively, as shown in embodiments in FIGS. 6 and 7, the internal/external rotation pivot hub 1 may be a ball 1a, and the hub base plate 3 may be a socket base 3a. A ball joint (or similar mechanism) can be utilized for infinite adjustability. In one embodiment, locking the ball to the socket base 3a relies on the friction interface between the two surfaces. By adding a more aggressive "bite" from one surface to the adjacent, the hold will increase significantly.

Figure 7:
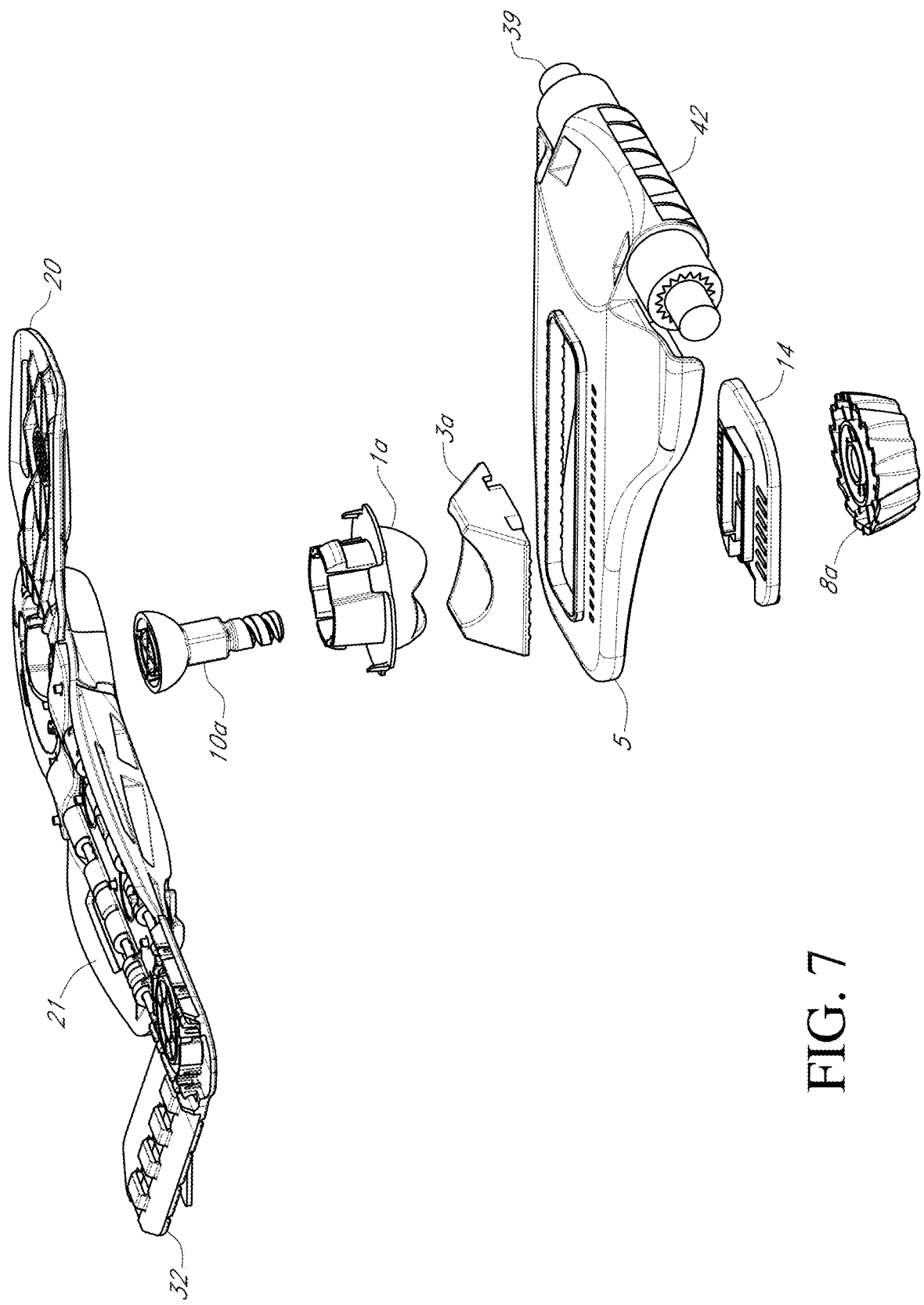
FIG. 7 illustrates an exploded view including a ball and socket interface, according to some example embodiments.
Figure 8:
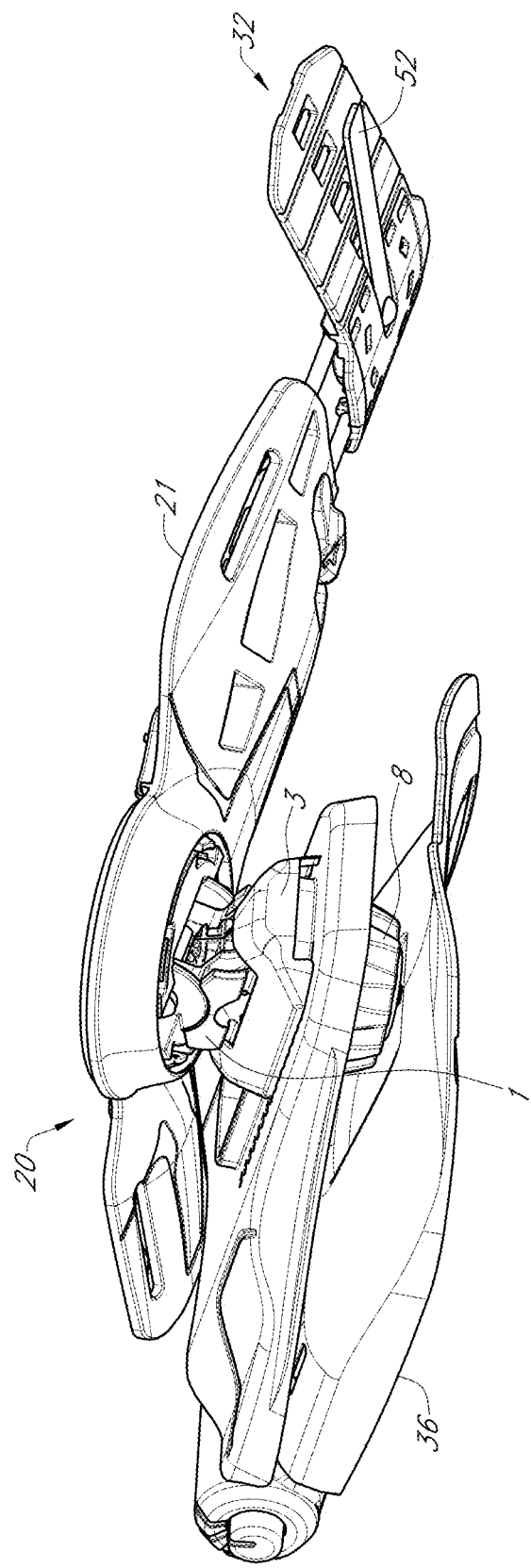
FIG. 8 illustrates a perspective view including a pivot interface, according to some example embodiments.

FIG. 7 illustrates an embodiment where the hub lock knob 8 is a locking torque knob 8a, and the hub lock down 10 is a lock down screw 10a. When in use, in some aspects, the internal/external rotation pivot hub 1 pivotally engages the hub base plate 3 and is lockable at any one of a plurality of predetermined indexing points or friction interface, by using the hub lock knob 8, such as the locking torque knob 8a. In some aspects, the rotation is about 45° from neutral in either the internal or external rotation therefore the entire swing may be about 90°. In additional aspects, locking torque knob 8a can be replaced with another hub lock mating member or other means of tightening the assembly, such as a screw/nut, cam lock, a compression spring holding mating gear together, or a ratcheting mechanism.

The hub base plate 3 may further comprise a slide member 13, as shown in FIG. 1. FIG. 1 also shows a panel 5, such as an abduction support panel 5a, that defines a panel opening 6 and has at least one hub base plate adjustment receiver 7 proximate the panel opening 6. A hub lock mating member such as a hub lock knob 8 defines a mating opening 9. Through the openings mentioned above, a hub lock down 10 is axially disposed, i.e., through the axial hub opening 2, the plate opening 4, and the panel opening 6. The hub lock down 10 comprises a mating end 11 mated to the mating opening 12 of the hub lock knob 8. The panel 5 is disposed between the hub base plate 3 and the hub lock knob 8. An assembly of the hub lock down 10, internal/external rotation pivot hub 1, hub base plate 3, and hub lock knob 8 is translatably engaged through the panel opening 6 of the at least one hub base plate adjustment receiver 7 of the panel 5. In this embodiment, the assembly allows the angle for the internal or external rotation of the forearm to be adjusted while simultaneously locking the selected arm length into position.

Figure 5:
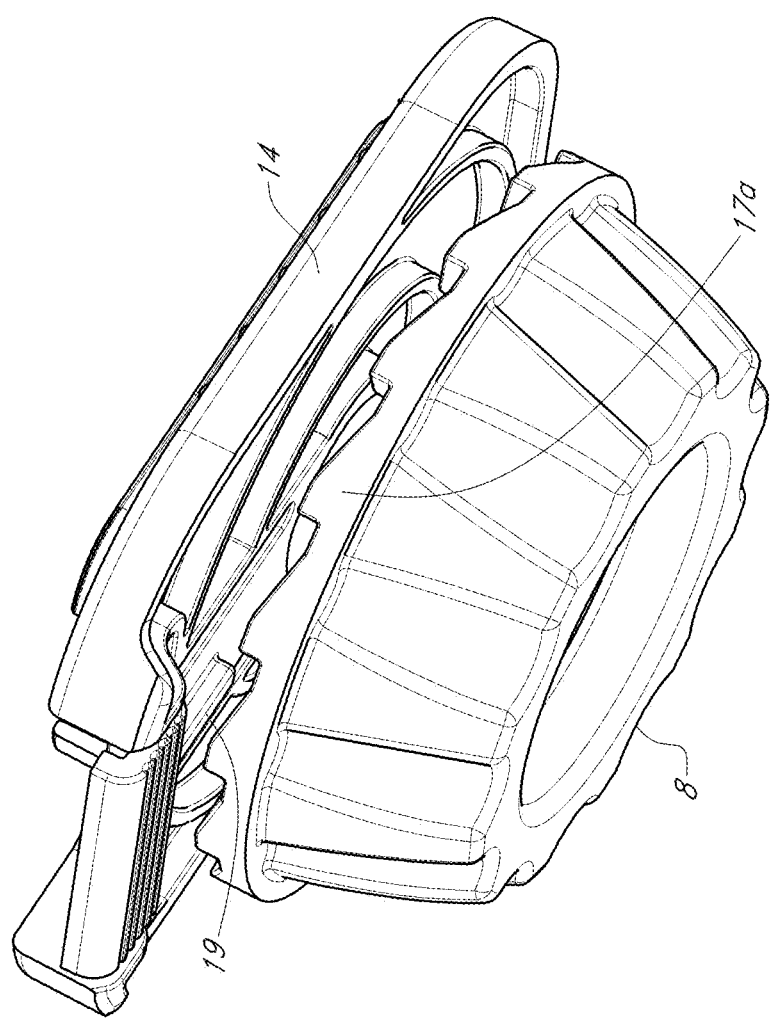
FIG. 5 illustrates a perspective view of a knob assembly, according to some example embodiments.

In one aspect, the hub lock knob 8 rotates freely, for example clock wise, to tighten the assembly. The lockable orthosis assembly may further comprise a lower hub washer 14 disposed between the panel 5 and the hub lock knob 8. FIG. 5 shows more detail of an aspect of the lower hub washer 14 and the hub lock knob 8, where the hub lock knob 8 further comprises uni-directional gear teeth 17a and the lower hub washer 14 has a key portion 19. In some aspects, the key portion 19 is integral to the lower hub washer 14. The key portion 19 of the lower hub washer 14 prevents the hub lock knob 8 from rotating, for example, counterclockwise freely (if the assembly was tightened clockwise) and lost the key portion 19 is depressed upward allowing the unidirectional gear teeth 17a of the hub lock knob 8 to rotate freely counterclockwise.

On the side of the hub lock knob 8 opposite the lower hub washer 14, the lockable orthosis assembly may further comprise a washer 15, which is proximate a distal end 16 of the hub lock knob 8, as shown in FIG. 1.

Methods of using the orthosis assembly include locking a position of the internal/external rotation pivot hub 1 in the hub base plate 3 at a selected angle; and sliding the at least one slide member 13 along the at least one hub base plate adjustment receiver 7 of the panel 5 to adjust for arm length.

The internal/external rotation pivot hub 1, may be positioned at angles from 0° to 90° or more and any degree or fraction of a degree in between. However, the limits of the material may necessitate a larger angle of change so that each tooth, for example retains its integrity without breaking. Infinite angles although possible, may not be practical based on the material used, such as a plastic that may break if the teeth that provide the angle are too thin.

Figure 2:
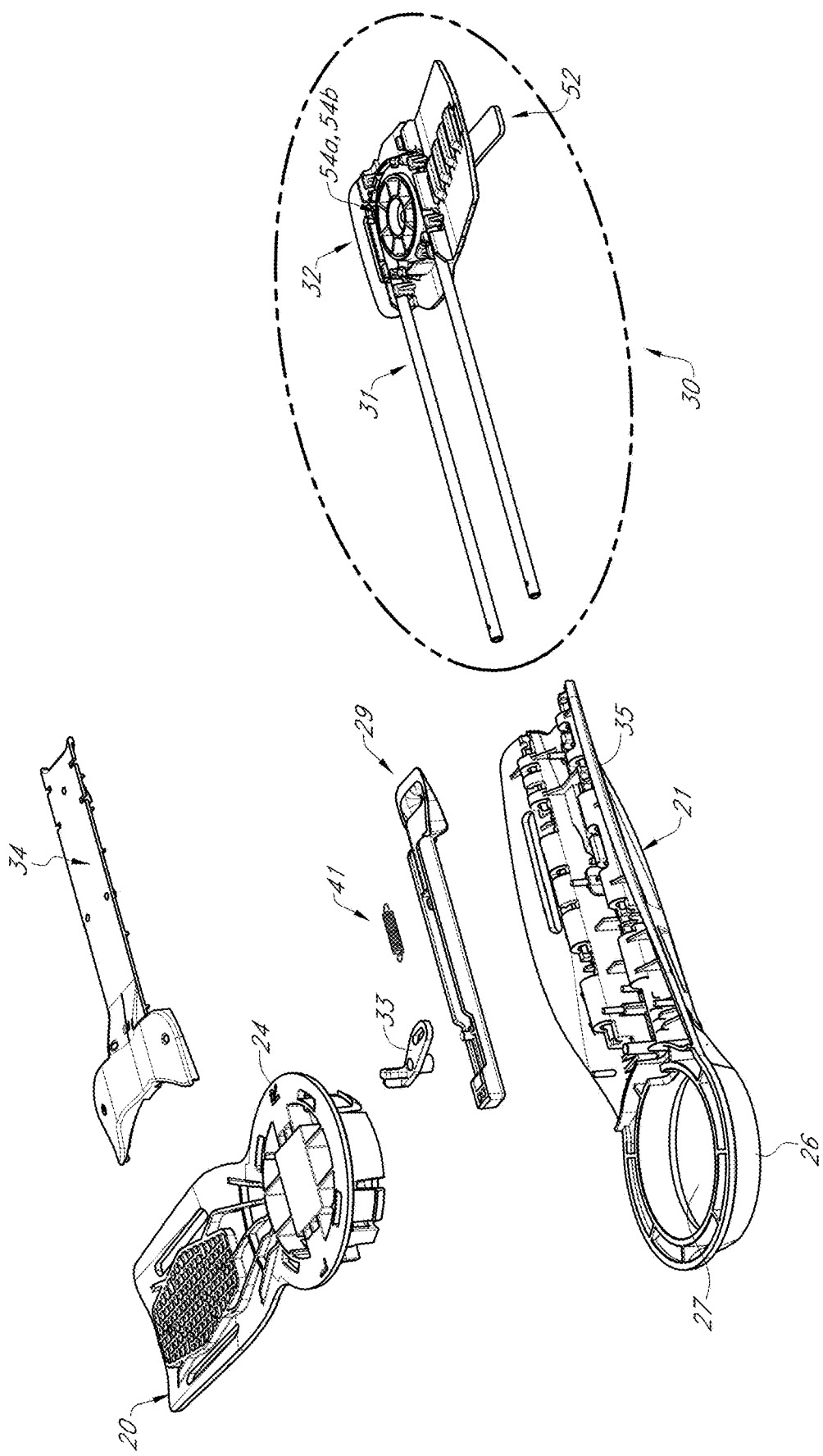
FIG. 2 illustrates an exploded view of the assemblies for the upper arm, forearm and wrists, including the rotating, according to some example embodiments.
Figure 3A:
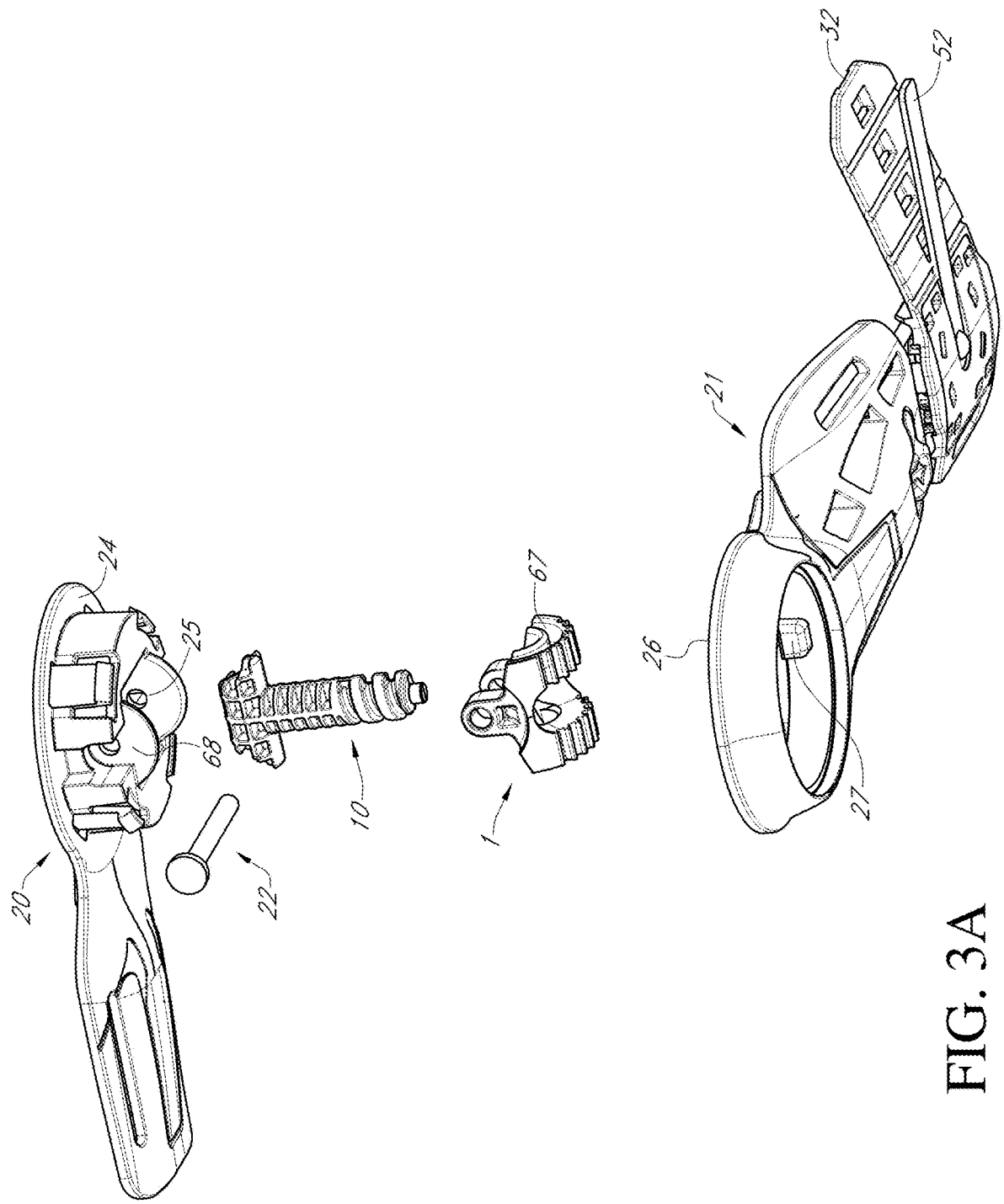
FIG. 3A illustrates an exploded view and partially exploded view 3B of an aspect of an orthosis assembly including the upper arm and forearm assembly, according to some example embodiments.

In some embodiments, the orthosis comprises a multi pivoting interface. The multi pivoting interface allows for alignment to patient anatomy and to preset the internal and external rotation of the patient's forearm. In some aspects, such as in FIGS. 2 and 3A, the multi pivoting interface comprises an upper arm support 20 coupled to the hub lock down 10; and a forearm support 21 rotationally engaged with the upper arm support 20 wherein at least a portion of the forearm support 21 is disposed between the upper arm support 20 and the internal/external rotation pivot hub 1. When in use, in some aspects, the arm brace pivots naturally in alignment to the elbow joint. Further, in some embodiments, for example, in FIG. 3B, the hub lock down 10 is at least partially recessed in the axial hub opening 2. FIGS. 1 and 3A show certain embodiments where the upper arm support 20 is coupled by a rivet 22 to the hub lock down 10. The assembly may also comprise, in some aspects such as shown in FIG. 2, a forearm cover 34 at least partially enclosing the arm brace lock 29 between the forearm cover 34 and a distal end 35 of the forearm support 21.

Figure 3B:
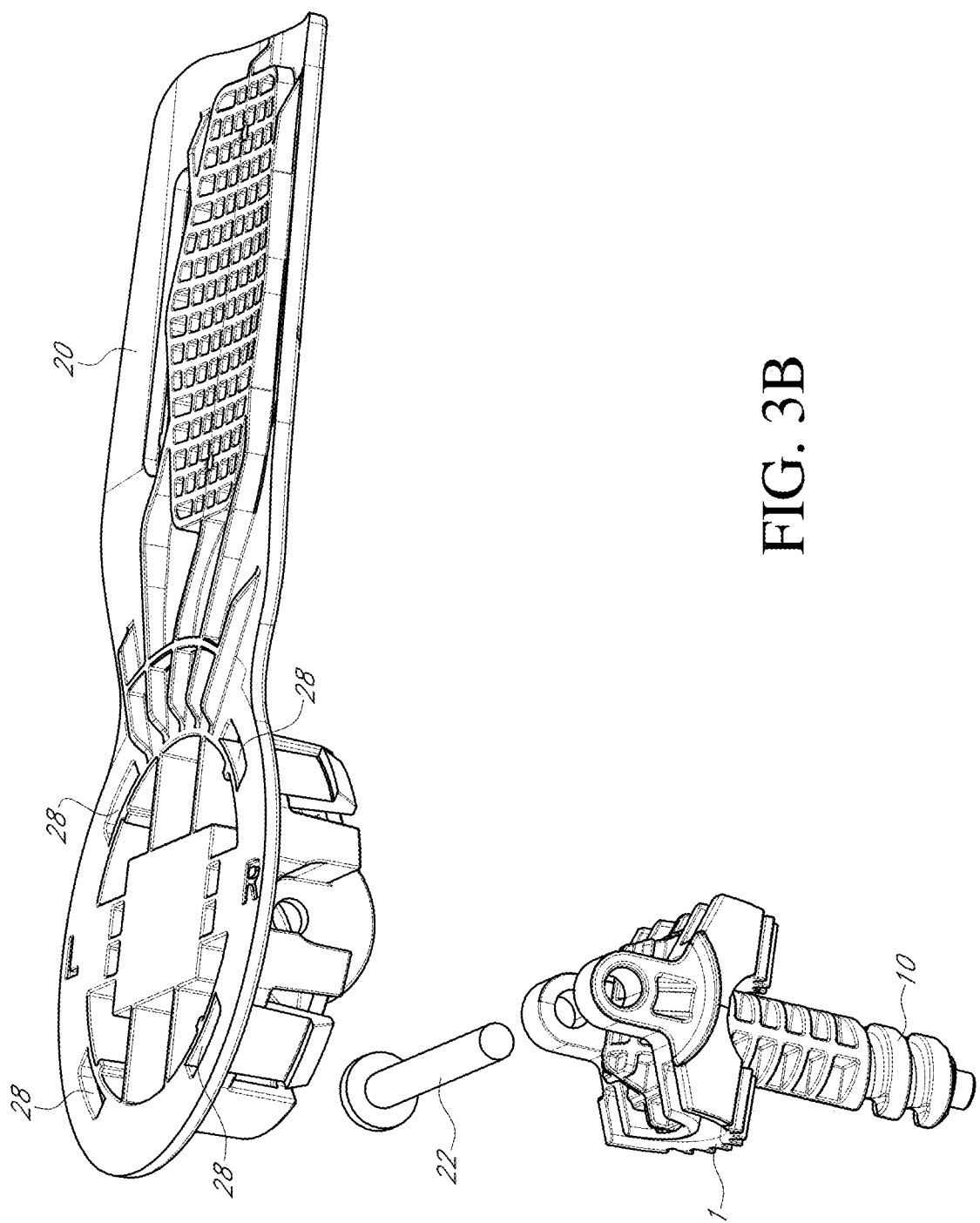

FIGS. 1, 3A and 3B also illustrate an embodiment wherein the internal/external rotation pivot hub 1 further defines at least one perpendicular hub opening 23; the upper arm support 20 having an upper arm support hub end 24 defining at least one perpendicular arm support opening 25; the at least one perpendicular hub opening 23 and the at least one perpendicular arm support opening 25 are aligned; and the rivet 22 is disposed through the at least one perpendicular hub opening 23 and the at least one perpendicular arm support opening 25.

In some aspects, the arm brace comprises a locking feature that locks the arm brace to the desired angular setting for normal daily use to provide support to the affected arm. The patient may disengage the lock on the brace to provide controlled flexion and extension of the arm as directed by a medical professional. The arm brace may be unlocked in various ways. For example, the arm brace may be unlocked using a lock switch on the brace.

The arm brace may be positioned for form an angle between the upper arm support 20 and the forearm support 21. In some aspects, the angles may be adjustable at least 180° to accommodate the position of a patient's left or right arm. Thus, the left or right arm may be positioned at neutral position (forearm is close to parallel to the sagittal plane and axial plane). Although the forearm at neutral is about 90° relative to the upper arm, in contrast, relative to neutral, the forearm would be positioned at 0° and would accommodate an angle of at least 180° from the neutral position to accommodate a right neutral arm position or a left neutral arm position depending on which arm the patient is treating, and in some aspects locks in place at 0° or 180° depending on the arm being treated. The angle may be adjusted at any degree or fraction of a degree at least in between 0° to 180°. In some aspects, the range of motion may also be accommodated by adding additional angles for flexion that may be adjusted such as 30-45° above neutral. When unlocked, the arm will hang down towards the floor when standing and may remain unlocked is some aspects. When unlocked, the forearm support can be moved in either direction and lock in neutral position.

FIG. 2 illustrates an embodiment comprising an arm brace lock 29 that may be longitudinally disposed within the forearm support 21. (The arm brace lock 29, in a different embodiment, may be in the upper arm support, however, the arm brace lock 29 may be easier to use when it is in the forearm support 21.) In one aspect, the forearm support 21 comprises a forearm support hub end 26 defining a forearm hub lock opening 27; and the upper arm support 20 comprises an upper arm support hub end 24 defining at least one arm support hub lock opening 28. The arm brace lock 29 may releasably engaged with the forearm support 21 through the forearm hub lock opening 27 and the upper arm support 20 through the at least one arm support hub lock opening 28.

Methods may include rotating the forearm support hub end 26 in relation to the upper arm support hub end 24 to position an angle between the upper arm support 20 and the forearm support 21; and locking the forearm support 21 at a selected angle. In some aspects, the orthosis is reversible and therefore the rotating step may further comprise accommodating an angle useful for the opposite arm.

Figure 4:
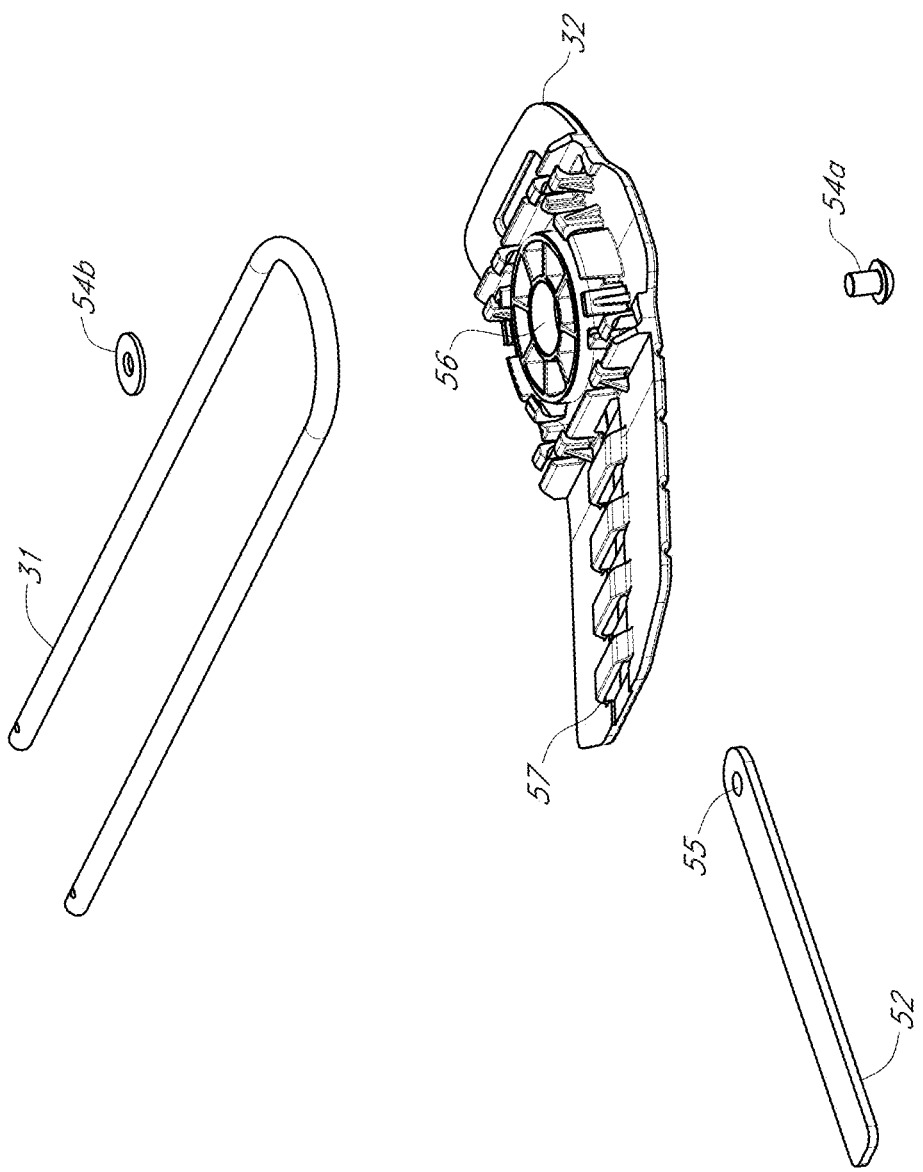
FIG. 4 illustrates an exploded view of a wrist assembly, according to some example embodiments.

Alternatively, or in addition, the arm brace may be unlocked by retracking a wrist support assembly 30 into the brace. FIGS. 2 and 4 show an aspect of the orthosis comprising a wrist support assembly 30 that may be adjustably engaged with the forearm support 21. The wrist support assembly 30 may comprise, in some aspects, at least one wrist bar 31 retractably engaged with the forearm support 21; and a wrist shell 32 removeably engaged with the at least one wrist bar 31. The locking aspect may also comprise a lock switch 33 being transversely aligned with the longitudinal axis of the at least one wrist bar 31 and moveably engaged with the arm brace lock 29. Thus, the lock switch 33 offers the patient the ability to quickly disengage the lock to allow for instant mobility. In some aspects, when the brace is returned to the initial setting (i.e., neutral setting, where the forearm is parallel to the sagittal and axial planes) the brace automatically re-locks into position. The re-tracked wrist support allows the patient to keep the arm brace unlocked for an extended period of time (to accommodate for exercise or longer activity) and will re-lock only when the wrist support is extended out of the retracted position. In some aspects, the telescoping wrist support provides support to the wrist during daily use and can be positioned to a desired length as required by the end user by adjusting the wrist support assembly 30 to a retracted or extended position. The wrist support may be retractable so lower arm exercises may be performed allowing for range of motion exercises.

The wrist support assembly 30 may further comprise, in some aspects, a stay 52 and a fastener 54, wherein the wrist shell 32 may be fastened to the stay 52 with the fastener 53, such as a rivet 54a and a washer 54b, as illustrated in the exploded view in FIG. 4. In some aspects, the stay 52 defines a fastener opening 55 and the wrist shell 32 defines a rivet opening 56 and a stay opening 57; wherein the rivet 54a is disposed through the fastener opening 55 of the stay 52 and the rivet opening 56. In use, the wrist shell 32 may be made from material such as polypropylene that may bend and conform to a patient's wrist, it may slowly lose its shape if left to flatten. The stay 52 such as a metal stay of aluminum or another bendable material may be also bend to shape around the wrist, but will retain its shape more than e.g. a polypropylene shell.

In some aspects, the wrist support comprises a removable interchangeable hand rest component that may be removed and rotated to accommodate either the left or the right wrist. For example, the wrist shell 32 may be configured to accept the wrist bar 31, which may snap in place in the wrist shell 32 in either direction, i.e., when the wrist shell 32 is rotated 180°.

In some aspects, the orthosis comprises a shoulder brace that may be positioned around the mid-torso region. In some embodiments, the pivoting alignment of the platform does not align with the shoulder joint. In some aspects, this offset allows the arm brace to align to the patient's arm independent of the platform angle. A semi-restricted movement is provided in the arm brace-frame interface to accommodate for this angle offset. More particularly, the internal/external rotation hub 1 may have semicircular slots 67 on either side for receiving semicircular members 68 from the upper arm support 20. This allows the upper arm support 20 to self align with the shoulder joint.

In some embodiments, the frame of the shoulder brace may comprise two loading platforms or panels, one (e.g., the panel 5 or abduction support panel 5a) may mechanically lock and support an arm brace and the other (e.g., the torso support panel 36) may be utilized as a leverage surface to support a position in space and rest on the torso. These platforms or panels may be made of various materials and may have various shapes. For example, the platforms may be rigid or semi-rigid and can be flat or in tubular form or may be molded. In some aspects, the torso support panel 36, may be made from trimmable material, may have prestressed regions, or break lines so that the panel may be cleanly broken, and therefore may be adjusted to fit various torso lengths and heights of patients. For example, in FIG. 1 the torso support panel 36, in some aspects, may comprise an alterable distal end 51.

The frame aids in the positioning of the arm brace relative to the patient's sagittal plane. In some aspects, the frame and arm brace are mechanically attached and the frame strategically transfers the load of the patient's arm to the torso. The frame may remain statically positioned on the patient's torso with the utilization of the garment, described below, and leverages this positioning to maintain stability of the shoulder while abducting, internally/externally rotating, and/or or while flexing or extending the forearm.

The frame may be made of various materials such as lightweight materials (for example, metals or plastics).

Figure 13:
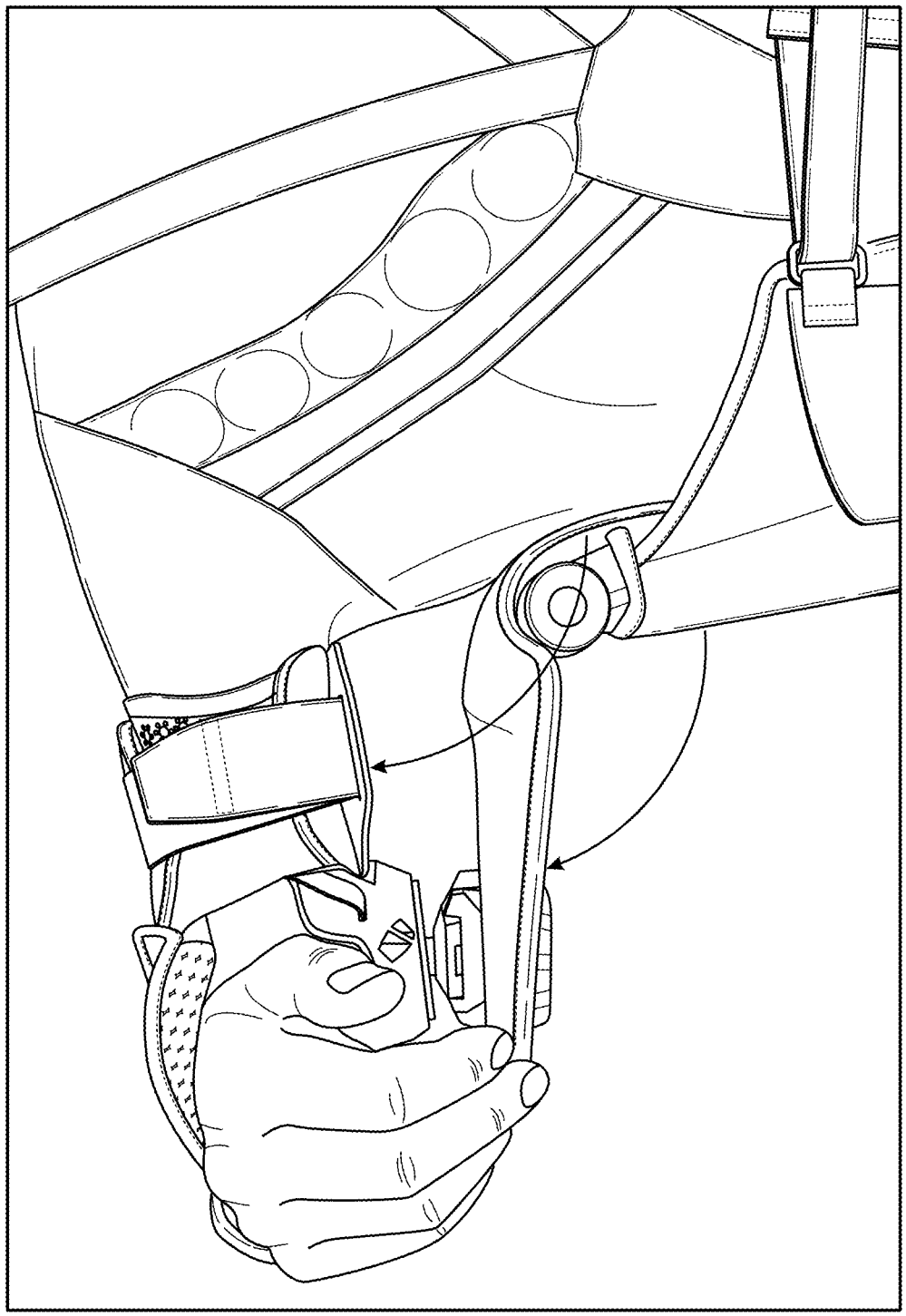
FIG. 13 shows an arm abduction angle between the torso and the supper arm, and the brace angle between the torso support panel and the abduction support panel, according to some example embodiments. The hinge does not reach the armpit of the wearer and thus is more comfortable than conventional abduction apparatuses such as wedges that cause discomfort when the brace is in direct contact with the armpit.

When in use, the frame may be collapsible enough to allow the patient the ability to closely achieve 0° (neutral) abduction. In some embodiments, the pivoting angle of the frame sits horizontally below the natural pivoting center of the shoulder, and thus the frame may allow for angles larger than 90°, such as 110° to 120° (although it could be extended farther), if for example, a patient wears the brace lower on the torso, to allow the true abduction positioning of the shoulder joint of 90° as shown in FIG. 13. Allowing angles to be larger, although not prevented, may find few uses or benefits related to abduction, e.g., allowing for 180°.

In some aspects, the locking abduction hinge 37 is capable of locking into predetermined angles with the use of one or more positive lock hinges. Hinges that have pins or other hinges such as in US Pat. Publ. 2011/0314637 may also be used. The shoulder brace portion of the orthosis, in some aspects, may comprise rigid hinged frame comprising a panel 5 such as the abduction support panel 5a coupled to a torso support panel 36 through a locking abduction hinge 37, such as a positive locking hinge, for example, as shown in FIG. 1. In in one embodiment, the locking abduction hinge 37 comprises a torso hinge 38 releasably engaged with a lock shaft 39 on a first distal end 40a of the locking abduction hinge 37. The opposite side of the locking abduction hinge 37 may comprise a free rotation hinge [not shown] on a second distal end 40b of the locking abduction hinge 37. In some aspects, the torso hinge 38 and the lock shaft 39 are axially aligned with the free rotation hinge [not shown]; and at least a portion of a spring 41 axially disposed between the lock shaft 39 and the free rotation hinge [not shown]. In some aspects, the torso hinge 38 defines a torso hinge opening 46 and torso hinge opposing teeth 47; and the lock shaft 39 defines shaft teeth 44 engagingly coupled to the opposing edge teeth 45 and the torso hinge opposing teeth 47. In some aspects, the torso support panel 36 may define a right perpendicular opening 50a on a right end 48a of the torso support panel 36 and a left perpendicular opening 50b on a left end 48b of the torso support panel. The right torso hinge 38a further may define a right protrusion 49a disposed within the right perpendicular opening 50a. The free rotation hinge [not shown] further may define a left protrusion 49b disposed within the left perpendicular opening 50b.

More stable abduction may be achieved, for example, when the locking abduction hinge 37 comprises a right torso hinge 38a releasably engaged with a right lock shaft 39a on a right distal end 40a of the locking abduction hinge 37; and a left torso hinge 38b releasably engaged with a left lock shaft 39b on a left distal end of the locking abduction hinge 37, as shown in FIG. 1. The left torso hinge 38b and the left lock shaft 39b maybe axially aligned with the right torso hinge 38a and the right lock shaft 39a.

Further, in some aspects, at least a portion of at least one spring 41 (such as 2 springs) is axially disposed between the right lock shaft and the left lock shaft. One spring and one lock shaft may also be used.

Figure 9:
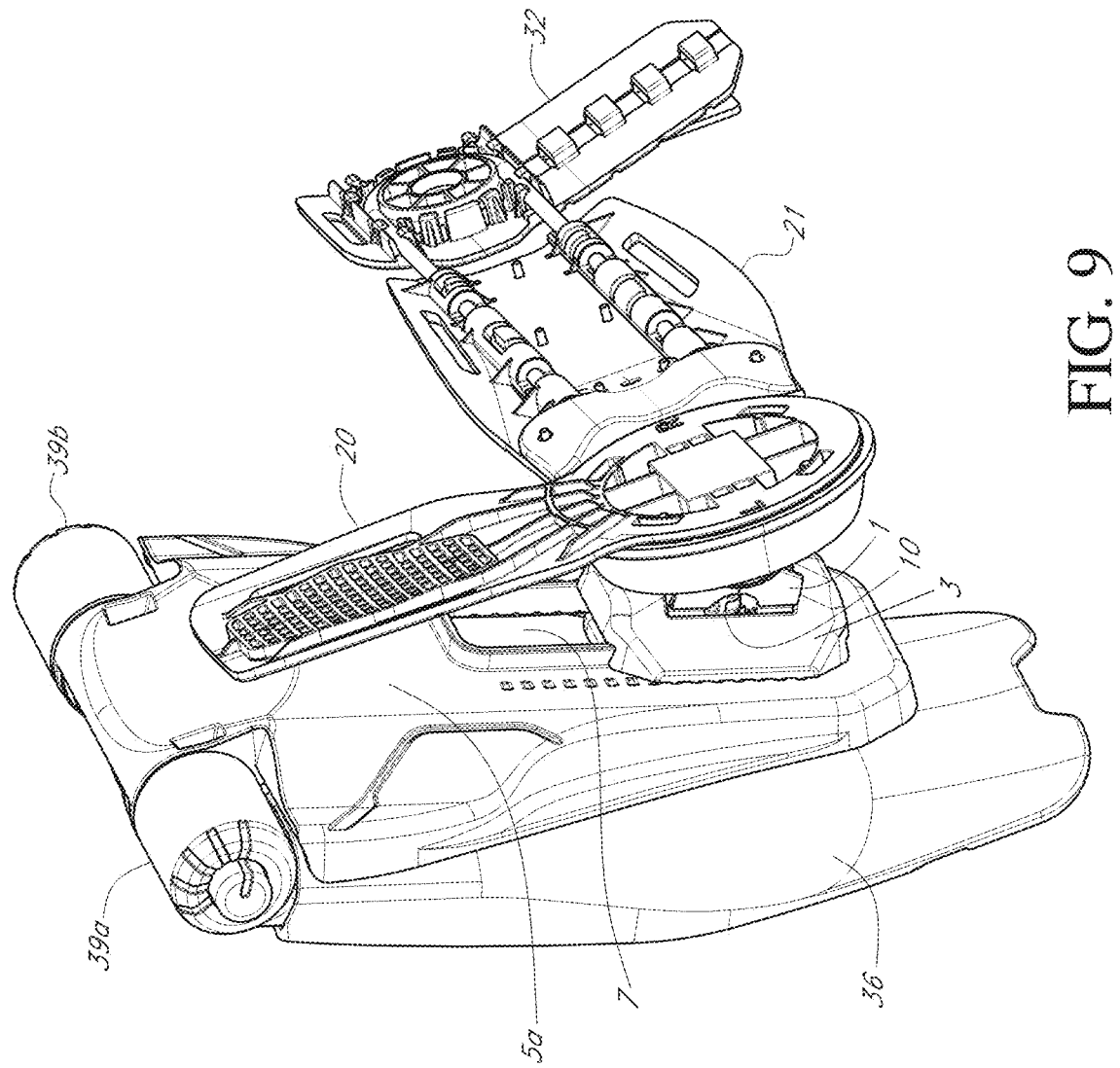
FIG. 9 illustrates a perspective view of an orthosis assembly, according to some example embodiments.

As shown in FIGS. 1 and 9, the locking abduction hinge 37 maybe located proximate an edge 42 of the abduction support panel 5 that defines an axial edge opening 43, that may be axially aligned with the lock shaft 39. The abduction support panel 5 may also define opposing edge teeth 45 on at least one end of the axial edge opening 43. In further embodiments, the edge 42 may define a right edge opening 43a and right opposing edge teeth 45a, and a left edge opening 43b and left opposing edge teeth 45b on each end of the axial edge opening 43. In some aspects, the torso hinge 38 may define a right torso hinge opening 46a and right torso hinge opposing teeth 47a, and a left torso hinge opening 46b and left torso hinge opposing teeth 47b. Further, a right lock shaft 39a may define right shaft teeth 44a engagingly coupled to the right opposing edge teeth 45a and the right torso hinge opposing teeth 47a; and a left lock shaft 39b may define left shaft teeth 44b engagingly coupled to the left opposing edge teeth 45b and the left torso hinge opposing teeth 47b. Some aspects, the torso support panel 36 may define a right perpendicular opening 50a on a right end 48a of the torso support panel 36 and a left perpendicular opening 50b on a left end 48b of the torso support panel 36. The right torso hinge 38a further may define a right protrusion 49a disposed within the right perpendicular opening 50a and the left torso hinge 38b further may define a left protrusion 49b disposed within the left perpendicular opening 50b.

When in use, for example, an individual may depress one or more of the center buttons to allow the hinge to index to the desired angular setting and releasing the button will allow the hinge to lock itself into position. Other similar types positive lock hinges can be used to accomplish this positioning.

Methods may include adjusting the locking abduction hinge 37; and locking the locking abduction hinge 37 at a selected angle between the abduction support panel 5 and the torso support panel 36.

In some embodiments, the brace accommodates different patient sizes and weights, and therefore has universal fit unlike conventional braces. By adjusting the straps and pads the brace can be easily sizes for different anatomies. In addition, some aspects, the brace may be easily switched from a left to right arm application with the adjustment of, for example, straps, pads and by adjusting the angles of the arm and wrist supports.

Figure 10:
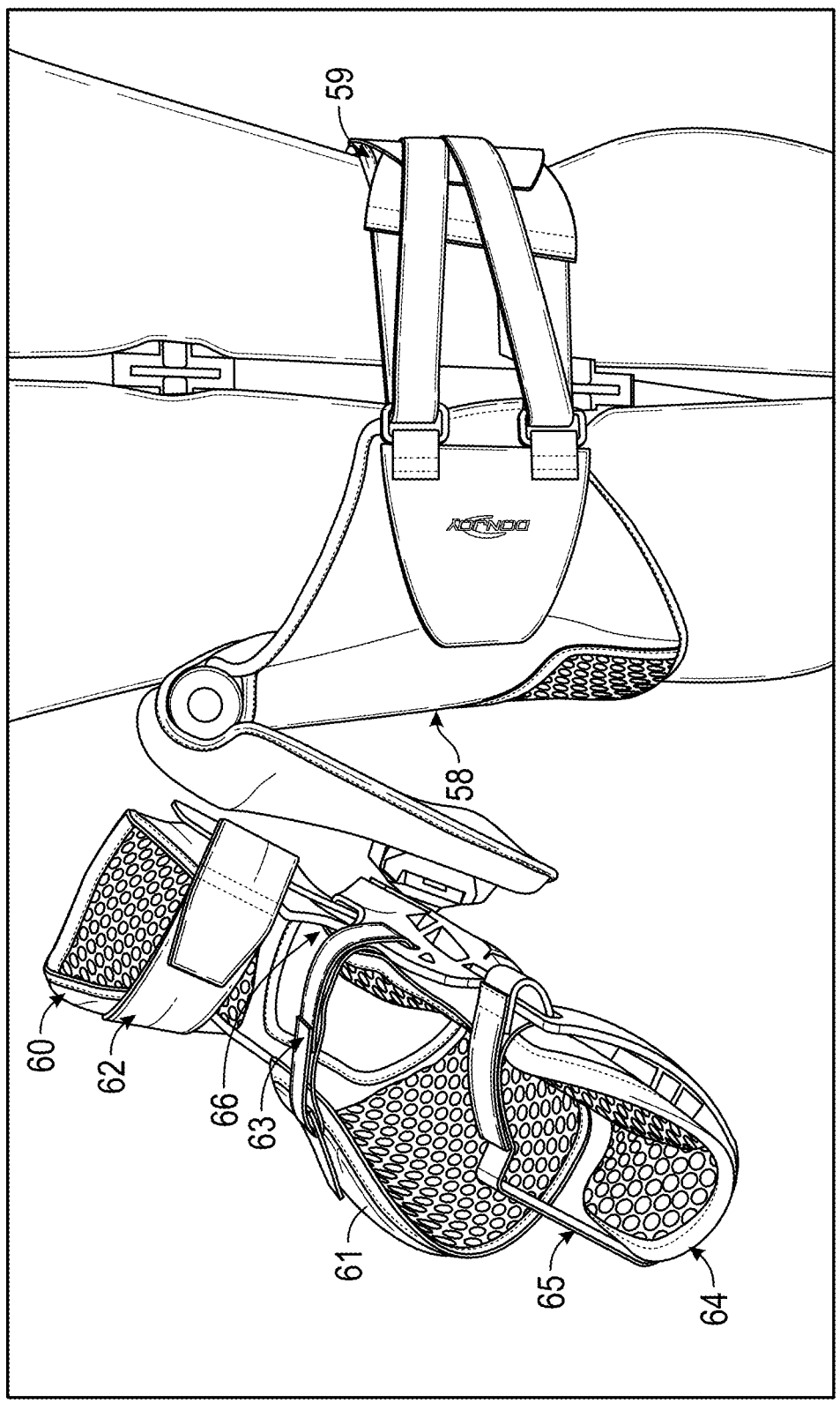
FIG. 10 illustrates a perspective view of an orthosis assembly with a garment that houses the assembly, according to some example embodiments.
Figure 11:
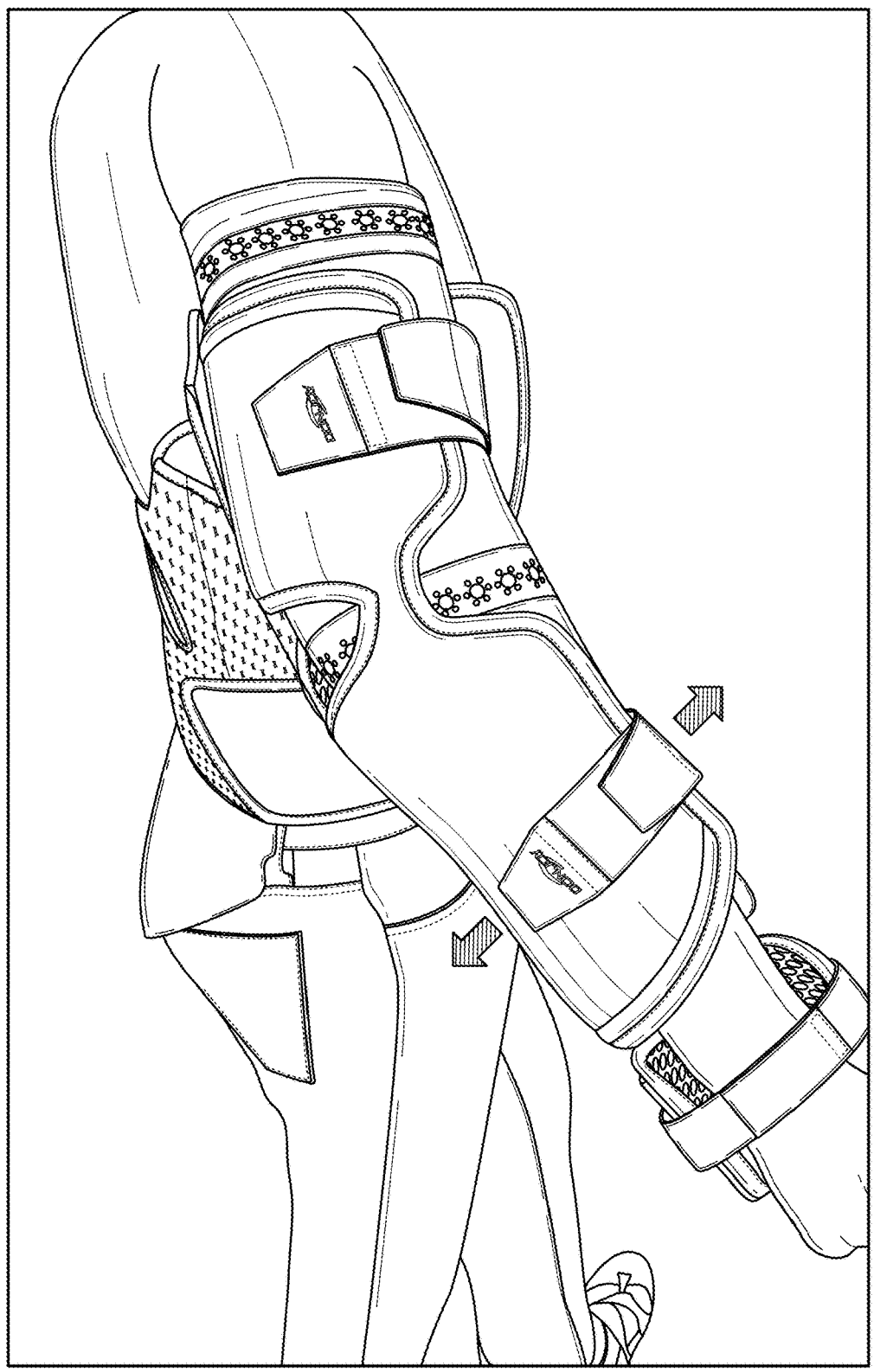
FIG. 11 illustrates the arm/brace pivot axis, where the arrows suggest the movement of the arm flexion and extension, according to some example embodiments.
Figure 12A:
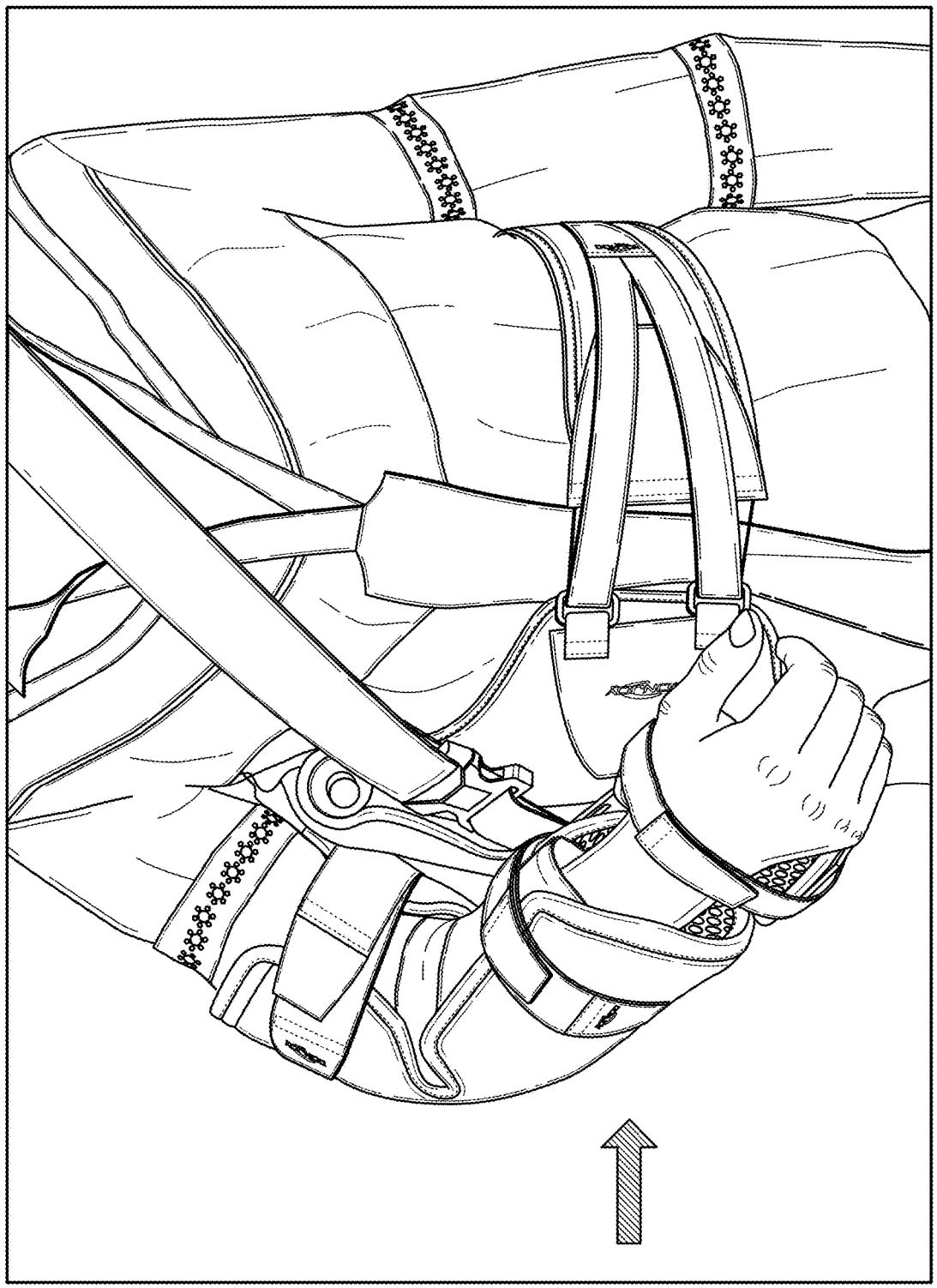
FIG. 12A illustrates internal rotation, according to some example embodiments.
Figure 12B:
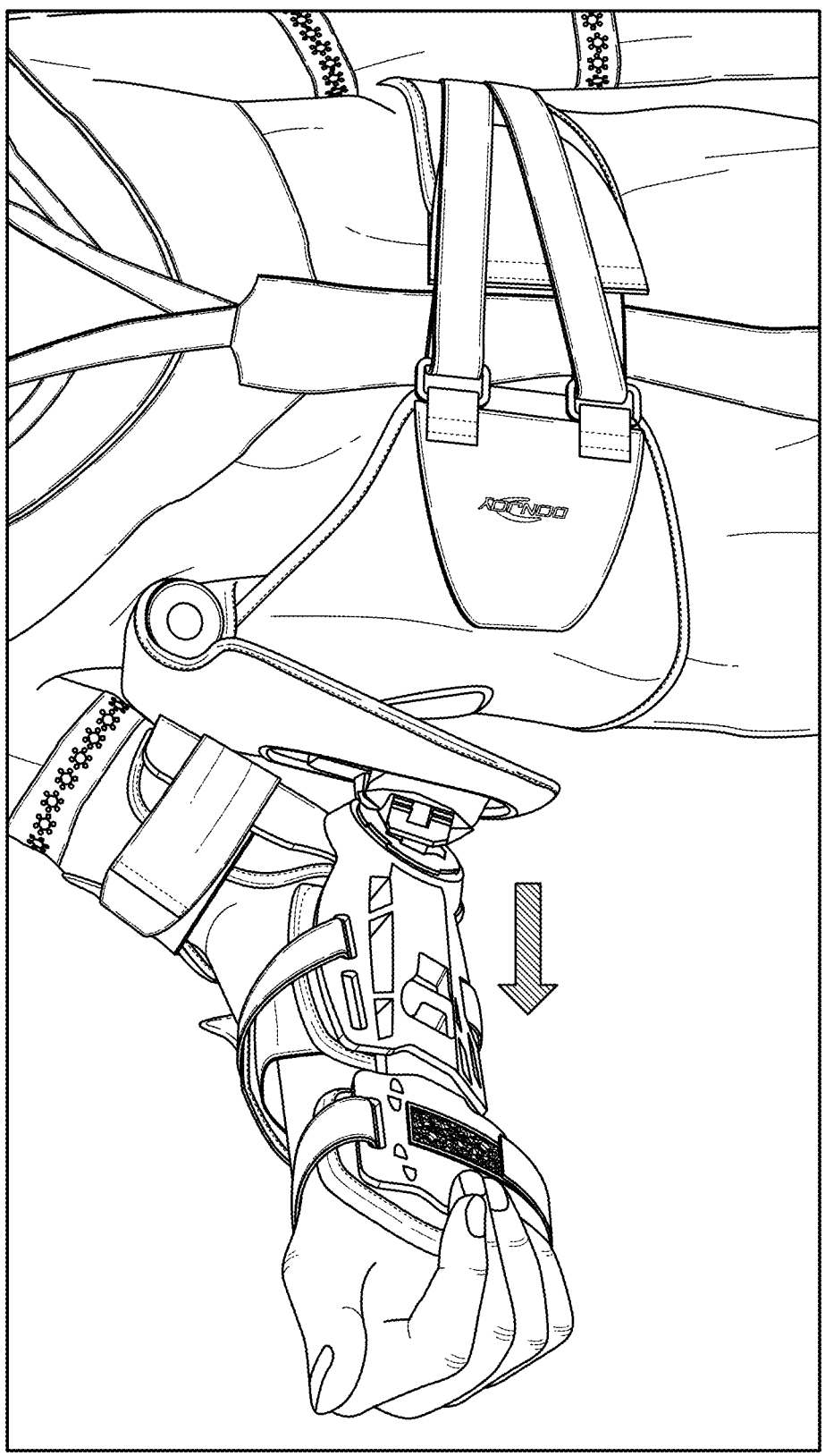
FIG. 12B illustrates external rotation, according to some example embodiments.

In some aspects, the orthosis comprises a rigid structural frame and arm brace enclosed within a garment meant to be strapped and secured around the patient's mid/lower torso. Comfortable padding enables the patient to don the brace for extended periods of time, inclusive of periods of rest or sleep. The brace may also incorporate an optional shoulder strap that may provide additional stability, weight distribution and/or additionally prevent product migration. In one embodiment, FIG. 10 shows a vest 58 at least partially enclosing the torso support panel 36 and has an adjustable belt 59.

To facilitate the user positioning the brace on the affected arm with the one remaining functional arm, the soft interface (or soft padding attached to the arm brace) may be lined with a malleable material so as to hold its shape (for example, at all times) and allow the end user to swiftly and with little effort slide the affected arm into the brace. In some aspects, sufficient padding is provided to prevent discomfort to the patient from this malleable material. The malleable material may be made of a bendable plastic or metal that can be positioned and hold its shape, such as a copper or aluminum wire or sheet having a sufficient gauge or strength to hold its shape but thin or flexible enough to bend.

In some embodiments, an arm brace comprises the upper arm support 20 and the forearm support covered with a soft interface that may encapsulate the upper arm and forearm to properly engage the patient's arm, for example, when it is attached to the shoulder brace. The arm may be secured using padding and straps. When desired, some aspects, the combination of strapping the arm in the arm brace and the frame to the torso, restricts motion of the shoulder joint and minimizes shoulder joint movement (retraction, protraction, depression, elevation). In one embodiment, FIG. 10 shows an upper arm support cover 60 at least partially enclosing the upper arm support 20; a forearm support cover 61 at least partially enclosing the forearm support 21; an upper arm securing member 62 secured to the upper arm support cover 60; and a forearm securing member 63 secured to the forearm support cover 61. The orthopedic shoulder device may also comprise a wrist assembly cover 64 at least partially enclosing the wrist assembly 30; and a hand securing member 65 secured to the wrist assembly cover 64.

In some aspects, the orthopedic shoulder device comprises a condyle cover 66 at least partially covering the upper arm support hub end 24 or the forearm support hub end 26 near the condyle area or the elbow. In some aspects, the condyle cover 66 is separate from the forearm support cover.

A liner or soft goods which line the arm rigid materials of the brace may be constructed from open or closed cell foam laminated with a moisture-wicking spacer fabric, polyethylene or EVA foam core, and/or a moisture wicking fabric laminated and/or breathable foam, and have sufficient padding so that the brace may be worn during sleep. The liners may be made from spacer fabric or breathable open cell foam such as post op knee liners, which may be made from polyurethane. Spacer fabric uses two separate fabrics, joined by microfilament yarn, to create a breathable, 3D "microclimate" between layers. The material may also include cooling portions or patches that pull heat away from the body.

The soft goods can be attached via fasteners, such as, snaps, plastic rivets or hook and loop fasteners.

The orthopedic shoulder brace is easy to use and may be positioned by a patient, using only the unaffected arm. In some aspects, once the abduction angle is set, the internal and external rotation angle is set, the arm length and/or the torso length is adjusted, the orthosis may be secured to the patient's body using only the unaffected arm.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

The word "othosis" or "orthotic" is used herein to mean a brace or other such device. Consequently, othosis may be used interchangeably with the term "brace" and may refer to specific types of braces when indicated (e.g., a shoulder orthosis or shoulder brace).

The orthosis or parts thereof, may be formed of one or more sturdy, rigid, lightweight materials, such as metal or water-resistant materials so that the orthosis can be used in a shower, bath, swimming pool, or other aqueous environment. The panels and/or supports or other components of the frame may be injection molded constructed from nylon, ABS, polypropylene, a combination of nylon and polypropylene, or other suitably strong plastic resin (e.g., polypropylene).

The word "neutral" is used herein to mean at or about zero degrees from a centermost position or plane. For example, with respect to forearm flexion or extension, neutral may refer to a plane roughly perpendicular to a user's spine. When positioning the arm from a user's body for abduction, neutral may refer to a plane roughly parallel to a user's spine.

"Strap" generally refer to one or more fasteners such as flexible straps, buckles, clips, clasps, fasteners such as hook and loop fasteners, or other detachable elements or may refer to a band that may grip a part of the anatomy. Hook and loop fastening systems (such as an array of loops) may mate with a corresponding component on a surface or may contain both mating components on a single strap. The straps in some aspects permit relatively rapid and easy attachment to and detachment. In some embodiments, the fasteners are coupled to the one or more portions of the frame panels by threading them through holes, e.g., in a panel or arm support.

Reference throughout this disclosure to "an embodiment" or "the embodiment" or an aspect thereof means that a particular feature, structure or characteristic described in connection with that embodiment is included in at least one embodiment. Thus, the quoted phrases, or variations thereof, as recited throughout this disclosure are not necessarily all referring to the same embodiment or aspect.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim in this or any application claiming priority to this application require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

While specific embodiments and applications of the present disclosure have been illustrated and described, it is to be understood that the disclosure is not limited to the precise configuration and components disclosed herein. Various modifications, changes, and variations which will be apparent to those skilled in the art may be made in the arrangement, operation, and details of the methods and systems of the present disclosure disclosed herein without departing from the spirit and scope of the disclosure.

What is claimed is:

1. A lockable orthosis assembly, comprising:
   an internal/external rotation pivot hub defining an axial hub opening;
   a hub base plate defining a plate opening, the hub base plate pivotally engaged with the internal/external rotation pivot hub;
   a rigid hinged frame comprising a panel coupled to a torso support panel through a locking abduction hinge, the panel defining a panel opening and having at least one hub base plate adjustment receiver proximate the panel opening;
   a hub lock knob defining a mating opening; and
   a hub lock down axially disposed through the axial hub opening, the plate opening, and the panel opening, the hub lock down comprising a mating end mated to the mating opening of the hub lock knob, wherein:
     the panel is disposed between the hub base plate and the hub lock knob; and
     an assembly of the hub lock down, the internal/external rotation pivot hub, the hub base plate, and the hub lock knob is translatably engaged through the panel opening of the at least one hub base plate adjustment receiver of the panel.

2. The lockable orthosis assembly of claim 1, wherein:
   the hub base plate further comprises a slide member; and
   the at least one hub base plate adjustment receiver is disposed proximate the hub lock knob.

3. The lockable orthosis assembly of claim 1, wherein the internal/external rotation pivot hub further defines a plurality of teeth pivotally engaged to a plurality of opposing teeth defined in the hub base plate.

4. The lockable orthosis assembly of claim 3, further comprising a lower hub washer having a key portion, wherein the hub lock knob further comprises uni-directional gear teeth.

5. The lockable orthosis assembly of claim 1, wherein:
the internal/external rotation pivot hub is a ball; and
the hub base plate is a socket base.

6. The lockable orthosis assembly of claim 1, wherein:
the hub lock knob is a locking torque knob; and
the hub lock down is a lock down screw.

7. The lockable orthosis assembly of claim 1, wherein, when in use, the internal/external rotation pivot hub pivotally engages the hub base plate and is lockable at any one of a plurality of predetermined indexing points or at a friction interface.

8. A multi pivoting interface, comprising:
a lockable orthosis assembly, comprising:
an internal/external rotation pivot hub defining an axial hub opening;
a hub base plate defining a plate opening, the hub base plate pivotally engaged with the internal/external rotation pivot hub;
a rigid hinged frame comprising a panel coupled to a torso support panel through a locking abduction hinge, the panel defining a panel opening and having at least one hub base plate adjustment receiver proximate the panel opening;
a hub lock knob defining a mating opening; and
a hub lock down axially disposed through the axial hub opening, the plate opening, and the panel opening, the hub lock down comprising a mating end mated to the mating opening of the hub lock knob,
wherein:
the panel is disposed between the hub base plate and the hub lock knob; and
an assembly of the hub lock down, the internal/external rotation pivot hub, the hub base plate, and the hub lock knob is translatably engaged through the panel opening of the at least one hub base plate adjustment receiver of the panel;
an upper arm support coupled to the hub lock down; and
a forearm support rotationally engaged with the upper arm support wherein at least a portion of the forearm support is disposed between the upper arm support and the internal/external rotation pivot hub.

9. The multi pivoting interface of claim 8, wherein:
the hub lock down is at least partially recessed in the axial hub opening; and
the upper arm support is coupled by a rivet to the hub lock down.

10. The multi pivoting interface of claim 8, wherein:
the internal/external rotation pivot hub further defines at least one perpendicular hub opening;
the upper arm support has an upper arm support hub end defining at least one perpendicular arm support opening;
the at least one perpendicular hub opening and the at least one perpendicular arm support opening are aligned; and
a rivet is disposed through the at least one perpendicular hub opening and the at least one perpendicular arm support opening.

11. The multi pivoting interface of claim 8, further comprising:
an arm brace lock longitudinally disposed within the forearm support; and
the forearm support comprises a forearm support hub end defining a forearm hub lock opening, wherein:
the upper arm support comprises an upper arm support hub end defining at least one arm support hub lock opening, and
the arm brace lock is releasably engaged with the forearm support through the forearm hub lock opening and the upper arm support through the at least one arm support hub lock opening.

12. The multi pivoting interface of claim 8, further comprising a wrist support assembly adjustably engaged with the forearm support.

13. The multi pivoting interface of claim 12, the wrist support assembly comprising:
at least one wrist bar retractably engaged with the forearm support; and
a wrist shell removeably engaged with the at least one wrist bar.

14. The multi pivoting interface of claim 13, further comprising a lock switch transversely aligned with the longitudinal axis of the at least one wrist bar and moveably engaged with an arm brace lock longitudinally disposed within the forearm support.

15. An orthopedic shoulder device comprising:
a multi pivoting interface comprising:
a lockable orthosis assembly comprising:
an internal/external rotation pivot hub defining an axial hub opening;
a hub base plate defining a plate opening, the hub base plate pivotally engaged with the internal/external rotation pivot hub;
an abduction support panel defining a panel opening and having at least one hub base plate adjustment receiver proximate the panel opening;
a hub lock knob defining a mating opening; and
a hub lock down axially disposed through the axial hub opening, the plate opening, and the panel opening, the hub lock down comprising a mating end mated to the mating opening of the hub lock knob, wherein:
the abduction support panel is disposed between the hub base plate and the hub lock knob; and
an assembly of the hub lock down, the internal/external rotation pivot hub, the hub base plate, and the hub lock knob is translatably engaged through the panel opening of the at least one hub base plate adjustment receiver of the abduction support panel;
an upper arm support coupled to the hub lock down; and
a forearm support rotationally engaged with the upper arm support wherein at least a portion of the forearm support is disposed between the upper arm support and the internal/external rotation pivot hub; and
a rigid hinged frame comprising the abduction support panel coupled to a torso support panel through a locking abduction hinge.

16. The orthopedic shoulder device of claim 15, wherein the locking abduction hinge is a positive locking hinge.

17. The orthopedic shoulder device of claim 15, wherein the locking abduction hinge comprises:
a torso hinge releasably engaged with a lock shaft on a first distal end of the locking abduction hinge;
a free rotation hinge on a second distal end of the locking abduction hinge, wherein the torso hinge and the lock shaft are axially aligned with the free rotation hinge; and at least a portion of a spring axially disposed between the lock shaft and the free rotation hinge.

18. The orthopedic shoulder device of claim 15, wherein the locking abduction hinge comprises:
a right torso hinge releasably engaged with a right lock shaft on a right distal end of the locking abduction hinge;
a left torso hinge releasably engaged with a left lock shaft on a left distal end of the locking abduction hinge, the left torso hinge and the left lock shaft are axially aligned with the right torso hinge and the right lock shaft; and
at least a portion of at least one spring axially disposed between the right lock shaft and the left lock shaft.

19. The orthopedic shoulder device of claim 17, wherein:
an edge of the abduction support panel defines an axial edge opening and opposing edge teeth on at least one end of the axial edge opening, the edge of the abduction support panel being axially aligned with the lock shaft;
the torso hinge defines a torso hinge opening and torso hinge opposing teeth; and
the lock shaft defines shaft teeth engagingly coupled to the opposing edge teeth and the torso hinge opposing teeth.

20. The orthopedic shoulder device of claim 18, wherein
an edge defines a right edge opening and right opposing edge teeth, and a left edge opening and left opposing edge teeth on each end of the axial edge opening;
the torso hinge defines a right torso hinge opening and right torso hinge opposing teeth, and a left torso hinge opening and left torso hinge opposing teeth;
a right lock shaft defines right shaft teeth engagingly coupled to the right opposing edge teeth and the right torso hinge opposing teeth; and
a left lock shaft defines left shaft teeth engagingly coupled to the left opposing edge teeth and the left torso hinge opposing teeth.

* * * * *